US00PP30388P3

(12) United States Plant Patent
Biancheri

(10) Patent No.: US PP30,388 P3
(45) Date of Patent: Apr. 16, 2019

(54) ***RANUNCULUS* PLANT NAMED 'ABSIRLPIN'**

(50) Latin Name: *Ranunculus asiaticus*
Varietal Denomination: ABSIRLPIN

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,519

(22) Filed: Jun. 20, 2017

(65) Prior Publication Data

US 2018/0368304 P1 Dec. 20, 2018

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
See application file for complete search history.

(56) References Cited

PUBLICATIONS https://flowerona.com/2014/04/a-fact-sheet-on-cloni-ranunculus/, Flowerona Inspired by Flowers, Apr. 10, 2014, pp. 1-8.*
https://www.bianchericreazioni.it/scheda-181-hanoi, Biancheri Creazioni Hanoi, p. 1, downloaded Jul. 26, 2018.*

* cited by examiner

*Primary Examiner* — Anne Marie Grunberg
(74) *Attorney, Agent, or Firm* — Cassandra Bright

(57) ABSTRACT

A new and distinct *Ranunculus* cultivar named 'ABSIRLPIN' is disclosed, characterized by flowers of a very light pink shade. Plants are and produce an above average quantity of flowers of high quality throughout the flowering season. Flower size produced remains large throughout the flowering season. The new variety is a *Ranunculus*, normally produced as a cut flower and potentially useful as an ornamental plant.

2 Drawing Sheets

Figure 1:
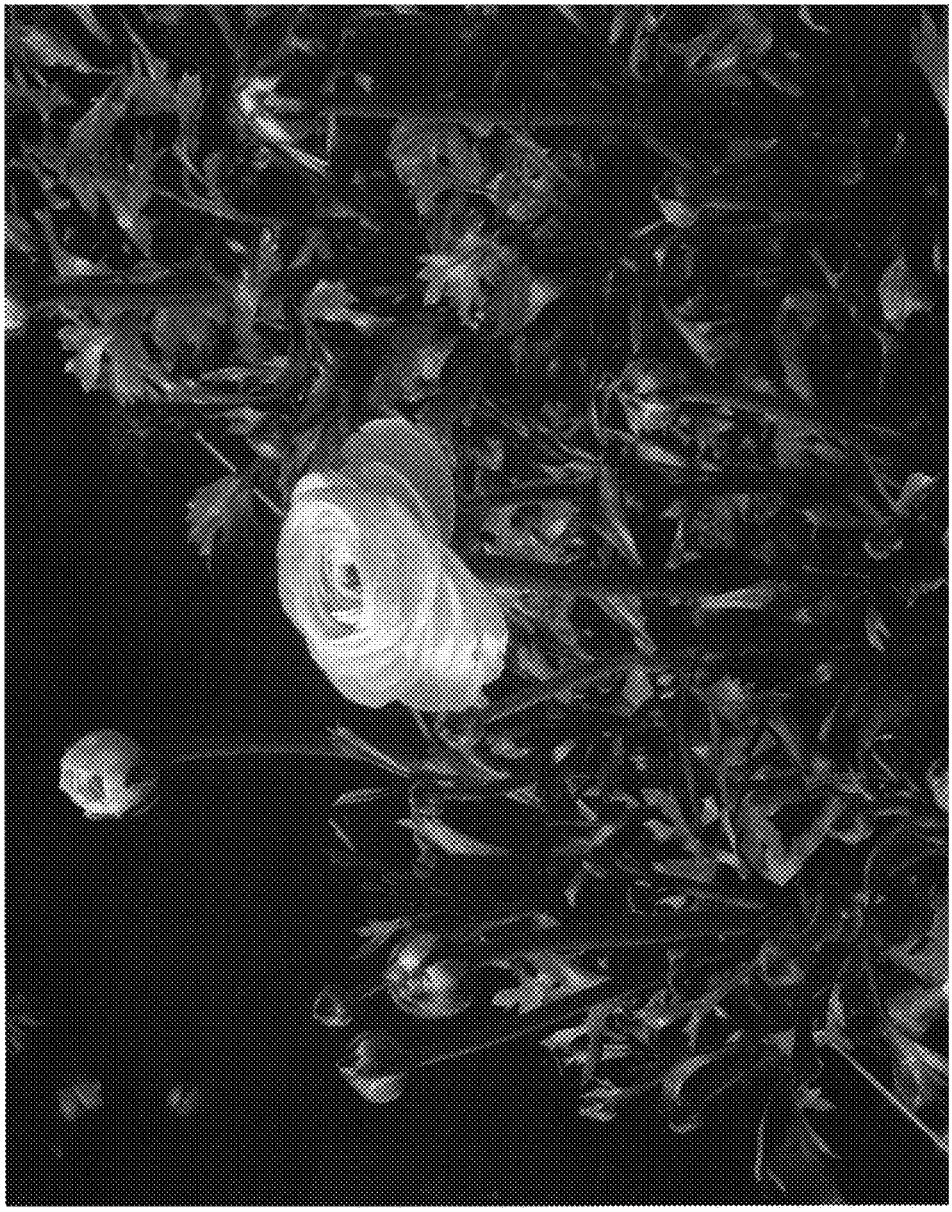

Latin name of the genus and species: *Ranunculus asiaticus*.

Variety denomination: 'ABSIRLPIN'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2011.

Parent varieties are both, unpatented, undistributed proprietary varieties of *Ranunculus asiaticus*. The new variety was discovered in 2014 by the inventor in a group of seedlings resulting from the 2011 crossing, in a research greenhouse in Camporosso Mare, Italy.

Asexual reproduction of the new cultivar was performed by vegetative division of buds sprouting from the rhizome of the selected plant. Subsequent propagation has been performed by tissue culture. First propagation took place at a research greenhouse in Camporosso Mare, Italy in 2014 and has shown that the unique features of this cultivar are stable and reproduced true to type in multiple successive generations.

SUMMARY OF THE INVENTION

The cultivar 'ABSIRLPIN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABSIRLPIN' These characteristics in combination distinguish 'ABSIRLPIN' as a new and distinct *Ranunculus* cultivar:

1. Exceptionally light pink flower color.
2. Large corolla production throughout the flowering season.
3. Exceptionally strong plants.
4. Above average quantity and quality of flower stems produced during the flowering season.

PARENT COMPARISON

Plants of the new cultivar 'ABSIRLPIN' are similar to plants of the seed parent, in most horticultural characteristics, however, plants of the new cultivar 'ABSIRLPIN' differ in the following;

1. The new variety has a different flower color. The new variety has a primary petal color of Red 49D, and a secondary color of Orange 27D. The seed parent has a single petal color of Red 38D.
2. Flower diameter of 'ABSIRLPIN' has an average range of 10 to 14 cm, flower diameter of the seed parent is on average in the range of 8 to 10 cm.

Plants of the new cultivar 'ABSIRLPIN' are similar to plants of the pollen parent, in most horticultural characteristics, however, plants of the new cultivar 'ABSIRLPIN' differ in the following;

1. The new variety has a different flower color. The new variety has a primary petal color of Red 49D, and a secondary color of Orange 27D. The pollen parent has a single petal color of Red-Purple N57D.
2. Flower diameter of 'ABSIRLPIN' has an average range of 10 to 14 cm, flower diameter of the pollen parent is on average in the range of 8 to 10 cm.

COMMERCIAL COMPARISON

Plants of the new cultivar 'ABSIRLPIN' are comparable to the unpatented commercial variety *Ranunculus* 'ABLIGHTPIN'. The two *Ranunculus* varieties are similar in most horticultural characteristics; however, the new variety 'ABSIRLPIN' differs in the following:

1. Flower color of the new variety is lighter pink.

BRIEF DESCRIPTION OF THE PHOTOGRAPHS

The accompanying photograph in FIG. 1 illustrates in full color flowering plants of the new variety at approximately five months old, grown in a greenhouse.

Figure 2:
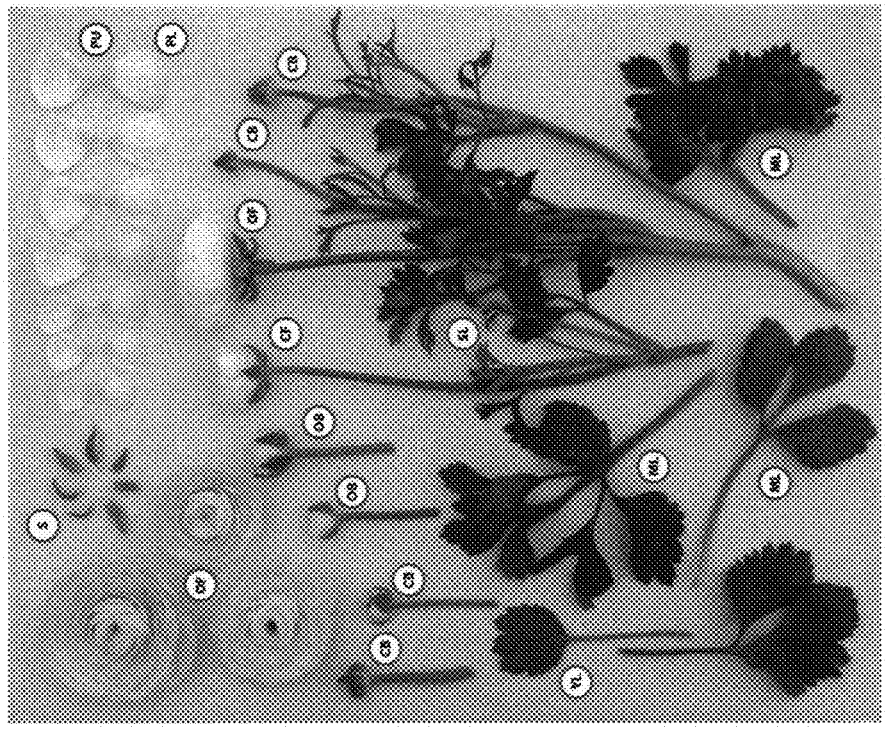

FIG. 2 illustrates a close up of plant parts. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABSIRLPIN' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABSIRLPIN'.

PROPAGATION

Time to rooting: 15 days at approximately 10-12° C.

Time to produce a rooted plantlet: 20 days.

Root description: Secondary roots grow from the rhizome and are fasciculate type.

PLANT

Growth habit: Herbaceous perennial, robust plant, semi-prostrate vegetation.

Height to top flower: 55 to 65 cm.

Plant spread: 50 to 60 cm.

Growth rate: Medium.

Branching characteristics: Simple or branched. Main floral stems grow from a basal rosette with 1 or 2 lateral branches, each one of which has 1 to 3 flowers.

Length of lateral branches: 45 to 50 cm.

Diameter of lateral branches: 0.5 to 0.7 cm.

Texture of lateral branches: Glossy, slightly tomentose.

Internode length: Internodes are extremely close together, forming a basal rosette.

Strength of lateral branches: Medium.

Color of lateral branches: Yellow Green (RHS 144A).

Angle of branches: 25° to 30°.

Number of leaves per lateral branch: Usually 2 or 4.

FOLIAGE

The leaves, usually numerous, have a marked heterophyllia, in relation to the degree of their development and their position on the plant (base of the plant; floral stem).

Leaf at the base of the plant:

*Arrangement.*—Simple to biternate (young leaf, YL); Biternate (mature leaf, ML).

*Average length.*—25 to 40 cm.

*Average width.*—14 to 24 cm.

*Overall shape of blade.*—Obovate (young leaf); Palmatipartite (mature leaf).

*Dissected leaves, describe lobes, quantity of dissection.*—Young leaves are generally not lobed; mature leaves are generally divided in 3 parts, each one of which is further divided in 3 or more lobes.

*Apex.*—Acute.

*Base.*—Acute.

*Attachment.*—Base of the plant.

*Margin.*—Dentate.

*Texture of top surface.*—Slightly tomentose.

*Texture of bottom surface.*—Slightly tomentose.

*Appearance of top surface.*—Glossy.

*Appearance bottom surface.*—Glossy.

*Leaf internode length.*—The internodes are extremely close together, forming a basal rosette.

*Color.*—Young foliage upper side: Green (RHS 137B). Young foliage under side: Green (RHS 139C to 139D). Mature foliage upper side: Green (RHS 137B). Mature foliage under side: Green (RHS 139C to 139D).

*Venation.*—Type: Dichotomous; plunging in to the limb at the upper surface; raised on the limb at the lower surface. Venation color upper side: Yellow Green (RHS 144A). Venation color under side: Yellow Green (RHS 144A).

*Petiole.*—Petiole: Long, tubular, rigid. Length: 18 to 23 cm. Diameter: 0.5 to 1.0 cm. Pubescence: Slightly tomentose. Color: Yellow Green (RHS 144A).

Leaf inserted at the nodes of the floral stems (sl):

*Arrangement.*—Biternate.

*Average length.*—20.0 to 25.0 cm.

*Average width.*—13.0 to 18.0 cm.

*Overall shape of blade.*—Palmatipartite.

*Dissected leaves, describe lobes, quantity of dissection.*—Generally divided in 3 parts, each one of which further divided in many deeply incised lobes.

*Apex.*—Acute.

*Base.*—Acute.

*Attachment*.—Floral stems.
*Margin*.—Dentate.
*Texture of top surface*.—Slightly tomentose.
*Texture of bottom surface*.—Slightly tomentose.
*Appearance of top surface*.—Matte.
*Appearance bottom surface*.—Glossy.
*Leaf internode length*.—8 to 12 cm.
*Color*.—Foliage upper side: Green (RHS 137A). Foliage under side: Green (RHS 139C to 139D).
*Venation*.—Type: Dichotomous, plunging in to the limb at the upper surface and raised on the limb at the lower surface. Venation color upper side: Yellow Green (RHS 144A). Venation color under side: Yellow Green (RHS 144A).
*Petiole*.—Petiole: Long, slightly flat, rigid. Length: 10 to 12 cm. Diameter: 0.6 to 1.2 cm. Pubescence: Slightly tomentose. Color: Yellow Green (RHS 144A).

FLOWER

Bloom period: Winter to Spring.
Vase life (cut flower): 10 to 15 days.
Persistent or self-cleaning: Self-Cleaning.
Bud:
*Closed bud* (*cb*).—Shape: Flattened globular with a sharp point. Length: 1.3 to 2.5 cm. Diameter: 1.0 to 2.5 cm. Color: Green (RHS 137C) at the center; Yellow Green (RHS 145B) where sepals start to overlap; Red Purple (RHS 71A) along the venations and near the base.
*Slightly open bud* (*ob*).—Shape: Flattened globular. Length: 2.0 to 2.8 cm. Diameter: 2.5 to 3.3 cm. Color: Orange (RHS 27D).
Flower size (of):
*Diameter*.—10 to 14 cm.
*Height*.—3.0 to 4.5 cm.
Corolla (of): Round, regular, in the form of a flat section.
Petals:
*Arrangement*.—Imbricated, disposed on the receptacle in very tight verticils. The size of the petals is quite variable, according to the position in the corolla, decreasing from the exterior toward the center. The average size of fully developed petal is as follows.
*Lobe length*.—2 to 6 cm.
*Lobe width*.—1 to 5 cm.
*Quantity*.—Double flower, petals are very numerous (>100).
*Texture*.—Silky, thin, resistant.
*Lobe apex*.—Rounded.
*Lobe shape*.—Obovate.
*Margin*.—Entire to Finely Crenate.
*Aspect*.—Obovate, concave with moderately reflexed apex when flower is fully opened.
Color when opening (cf):
*Upper surface*.—Orange (RHS 27D).
*Lower surface*.—Orange (RHS 27D).
Color fully opened (of):
*Upper surface* (*pu*).—Red (RHS 49D) to Orange (RHS 27D).
*Lower surface* (*pl*).—Red (RHS 49D) to Orange (RHS 27D).
Calyx to sepals (s):
*Quantity per flower*.—6 to 7.
*Shape*.—Concave, incurved at the apex.
*Length*.—4.4 to 7.0 cm.
*Width*.—4.4 to 5.5 cm.
*Apex*.—Slightly Acute to Rounded.
*Base*.—Flat.
*Margin*.—Entire.
*Texture*.—Lower surface is tomentose; Upper surface is glabrous.
*Color upper surface*.—Green (RHS 139C); Yellow Green (RHS 145B) at the base.
*Color lower surface*.—Green (RHS 137C); Red-Purple (RHS 71A) along the venations and Yellow Green (RHS 145B) near the base.
Peduncle: None.
Pedicel:
*Length*.—52 to 57 cm.
*Diameter*.—1.0 to 1.5 cm.
*Color*.—Yellow Green (RHS 144A).
*Orientation*.—Upright, straight, rigid.
*Pubescence*.—Slightly tomentose.
Fragrance: None.

REPRODUCTIVE ORGANS

Androecium:
*Stamens*.—Almost completely transformed as petals.
Gynoecium: The pistils are numerous, short, locked together at the center of the corolla in a Red Purple (RHS 59A) to Purple (RHS N79B) dome-shaped apocarpous gynoecium.

OTHER CHARACTERISTICS

Seeds and fruits: Seeds and fruit production not observed.
Disease topest resistance: Neither resistance nor susceptibility to normal diseases and pests of *Ranunculus* has been observed.
Temperature tolerance: Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABSIRLPIN' as herein illustrated and described.

* * * * *